United States Patent [19]

Molinski et al.

[11] 4,042,677

[45] Aug. 16, 1977

[54] TECHNETIUM-99M LABELED RADIODIAGNOSTIC AGENTS AND METHOD OF PREPARATION

[75] Inventors: Victor Joseph Molinski, Ridgewood, N.J.; Joseph Arthur Wilczewski, Newburgh, N.Y.

[73] Assignee: Union Carbide Corporation, New York, N.Y.

[21] Appl. No.: 636,372

[22] Filed: Dec. 1, 1975

Related U.S. Application Data

[63] Continuation-in-part of Ser. No. 501,704, Aug. 29, 1974, Pat. No. 3,987,157.

[51] Int. Cl.$^2$ .................... A61K 29/00; A61K 43/00; G01T 1/161; G21H 5/02
[52] U.S. Cl. ...................................... 424/1; 128/2 A; 250/303; 252/301.1 R; 424/9; 424/359
[58] Field of Search ................. 424/1, 1.5, 9, 359; 252/301.1 R; 128/2 A

[56] References Cited

U.S. PATENT DOCUMENTS

| | | | |
|---|---|---|---|
| 3,862,299 | 1/1975 | Bruno et al. | 424/1 |
| 3,872,226 | 3/1975 | Haney et al. | 424/1 |

OTHER PUBLICATIONS

Eckelman et al., Journal of Nuclear Medicine, vol. 12, No. 11, 1971, pp. 707–710.

*Primary Examiner*—Benjamin R. Padgett
*Assistant Examiner*—Christine M. Nucker
*Attorney, Agent, or Firm*—Israel Blum

[57] ABSTRACT

A method of preparing improved technetium-99m labeled radiodiagnostic agents by reducing technetium-99m with stannous tartrate. Such radiodiagnostic agents are useful in scintigraphic examinations of the bone and lung.

19 Claims, No Drawings

TECHNETIUM-99M LABELED RADIODIAGNOSTIC AGENTS AND METHOD OF PREPARATION

RELATED APPLICATIONS

This application is a continuation-in-part application of U.S. patent application Ser. No. 501,704, filed Aug. 29, 1974, now U.S. Pat. No. 3,987,157

FIELD OF THE INVENTION

This invention relats to improved technetium-99m labeled radiodiagnostic agents useful in lungs and bone scanning applications and a method for their preparation. This invention also relates to improved technetium-99m labeled radiodiagnostic agents useful in the scanning of the brain and blood pool and in cardiac studies. In another aspect, this invention relates to non-radioactive carriers employing stannous tartrate as a reducing agent and a process for their preparation.

DESCRIPTION OF THE PRIOR ART

Technetium-99m has become an extremely useful tool in medical applications, particularly as a radionuclide tracer in both medical research and diagnosis. Technetium-99's short half-life (6 hours) reduces exposure of the organs to radiation; its gamma radiation energy (140 Kev.) not only provides sufficient tissue penetration but also is readily collimated; and absence of beta radiation permits millicurie amounts of the radionuclide to be administered orally or by injection into the patient without harmful radiation dosage. Due to these physical characteristics, technetium-99m is frequently used in combination with appropriate carriers for in vivo diagnostic tests such as scrintigraphic examinations of the liver, lungs, blood pool, bone and tumors. Because no operation is required for diagnosis, the popularity of this method has increased in recent years.

Chemically, technetium belongs to group VII-A of the Periodic Table of the Elements and there are many similarities between its chemistry and the chemistry of manganese and rhenium. In aqueous solution, the most stable form of technetium is the pertechnetate ion ($TcO^-$), which is similar to iodide in its biological distribution, thereby rendering it useful in scanning. Moreover, the ability of technetium to combine with other materials when reduced to lower oxidation states makes it useful both when chelated with an appropriate carrier for kidney or blood function studies and also when trapped physically as a colloid for liver studies or as a particle for lung studies. Since technetium-99m has such a short half-life, it is commonly extracted from its parent element, 2.7 day molybdenum-99, as required, via a generator wherein $^{99m}Tc$ is eluted from $^{99}Mo$. Moreover, technetium in the form of sodium pertechnetate in an isotonic saline solution is generally mixed with an appropriate carrier to label it for use in various scintigraphic examinations.

Various processes of preparing diagnostic agents labeled with technetium-99m have employed ferric chloride, ferrous sulfate, ferrous ascorbate, stannous chloride, stannous chloride and streptokinase or urokinase, including a combination of components such as gelatin, sodium thiosulfate, sodium perrhenate and an inorganic acid. In some of these processes, the non-radioactive carrier prepared had a relatively short shelf-life. This required each medical facility to maintain facilities and personnel to prepare the tracer material. Non-radioactive chelates, in particular diethylenetriaminepentaacetic acid (DTPA), human serum albumin (HSA) and acid citrate dextrose (ACD) having an extended shelf-life, have been prepared employing stannous chloride as a reducing agent.

SUMMARY OF THE INVENTION

It is an object of this invention to provide a method of preparing technetium-99m labeled radiodiagnostic agents well suited for lung and bone scanning applications. It is also an object of this invention to provide a technetium-99m labeled radiodiagnostic agent which can be used for imaging the blood pool and for dynamic studies of the brain and heart. Another object of this invention is to provide a method of preparing non-radioactive carriers employing stannous tartrate. It is also an object of this invention to provide a stable blood pool agent containing stannous tartrate and human serum albumin and a method for its preparation. Another object of this invention is to provide non-radioactive serum albumin combined with stannous tartrate that is superior to serum albumin combined with stannous chloride. Still another object is to provide a simple and economical method of preparing non-radioactive carriers having a long shelf-life and which are useful in the preparation of technetium-99m labeled radiodiagnostic agents. Still another object is to provide a simple and economical process for the preparation of serum albumin carriers having a long shelf-life and useful intermediates in the preparation of technetium-99m labeled serum albumin. This and other objects will readily become apparent to those skilled in the art in the light of the teachings herein set forth. This invention is based on the discovery that stannous tartrate provides a superior reducing agent in the preparation of labeled technetium compounds and non-radioactive carrier precursors useful in preparing the technetium labeled compounds.

It has been discovered that stannous tartrate provides a superior labeling and reducing agent in the preparation of $^{99m}Tc$ labeled human serum albumin. Stannous tartrate is contacted with a solution of human serum albumin (herein after referred to as HSA) to form a non-radioactive carrier solution when the stannous tartrate has fully chelated. To form $^{99m}Tc$ HSA, the non-radioactive carrier in the solution or in lyophilized form comprising HSA stannous tartrate is contacted with $^{99m}Tc$ in the form of the pertechnetate ion, $NaTcO_4$ in normal saline solution.

A characterizing feature of the method of this invention is contacting stannous tartrate with a sequestering agent selected from the group consisting of a phosphoruscontaining compound which contains a P—O—P linkage and a diphosphonate which contains P—C—P bonds. Such sequestering agents provide suitable bone scanning agents after tagging with $^{99m}Tc$ and include the following phosphorus-containing compounds: (a) inorganic phosphates such as sodium pyrophosphate, sodium tripolyphosphate, sodium orthophosphate, sodium polyphosphate and the like, and (b) organic phosphonates such a 1-hydroxyethylidene-1, 1-disodium phosphonate, sodium methylene diphosphonate, the mono substituted salts of sodium methylene diphosphonate or sodium dichloromethylene diphosphonate, 1-hydroxyethylidene-1-mono-sodium phosphonate and the like. A particularly preferred organic phosphonate compound from this groups is 1-hydroxyethylidene-1, 1-disodium phosphonate (hereinafter referred to as HEDSPA).

The method of this invention is also characterized when stannous tartrate is contacted with human serum albumin in forming the non-radioactive carrier, macroaggregated albumin (hereinafter referred to as MAA). MAA is a particle formed containing stannous tartrate. In preparing the $^{99m}$Tc-labeled sequestering agent such as $^{99m}$Tc-labeled HEDSPA or the $^{99m}$Tc-labeled MAA, the non-radioactive carrier comprising the sequestering agent and stannous tartrate, e.g., HEDSPA-stannous tartrate, or MAA-stannous tartrate is contacted with $^{99m}$Tc contained in the form of pertechnetate ion from NaTcO$_4$ in normal saline solution.

MAA or sequestering agents such as HEDSPA ordinarily will not complex with technetium as pertechnetate but will complex with a tin-reduced pertechnetate. In the method of this invention by use of stannous tartrate, technetium may be reduced from a +7 oxidation state to a lower oxidation state suitable for complexing with technetium as pertechnetate. Moreover, the use of stannous tartrate provides a non-radioactive carrier more stable to oxidation as well as being suitable for mixing with a complexing agent. Generally, stannous compounds are easily oxidized to stannic compounds in aqueous solution. Moreover, in the absence of strongly complexing anions, tin having a +2 oxidation state is extensively hydrolyzed in aqueous solution. The hydrolyzed and oxidized compounds of tin formed in aqueous solution produce insoluble compounds. These insoluble compounds prevent the reaction of tin in the preparation of a radiodiagnostic agent and such agent would go to the lungs or liver metabolically thus interfering with diagnostic applications. This problem has been overcome by the use of stannous ion chelated with tartrate. By chelating with tin, tartrate substantially prevents deleterious oxidation of tin and the formation of stannous ions in solution. Otherwise oxidants such as peroxides, hydroxide radicals and the like, formed as a result of radiolysis, would consume ionized tin. In the method of this invention, however, this is prevented by employing stannous tartrate which is not strongly ionized in aqueous solution whereas stannous chloride is.

Another application of this principle has been in the preparation of an improved human serum albumin kit useful for blood pool scanning and dynamic studies of the brain and heart. By preventing hydrolysis the use of stannous tartrate produces a reagent which stays in the blood stream and does not produce colloidal tin particles which can trap the $^{99m}$Tc causing a large liver uptake. Stannous tartrate, in addition, provides a longer shelflife and permits the lyophilization of the product since it is stable and not subject to oxidation or radiolysis.

It has been found that stannous tartrate may be beneficially employed in the preparation of an improved MAA particle useful in lung scanning. Since the employment of stannous tartrate prevents hydrolysis, a more consistent MAA particle may be prepared. The MAA particle has fewer colloidal tin particles which can trap $^{99m}$Tc and cause an undesirable large liver uptake. Furthermore, the macroaggregated particle prepared according to this invention has a remarkably uniform particle size which gives superior lung to liver ratios. Additionally, the use of stannous tartrate in the method of this invention provides non-radioactive carrier solutions, such as HEDSPA-stannous tartrate and MAA-stannous tartrate, which have a long shelf-life since they are very stable and substantially not subject to oxidation or radiolysis when labeled with technetium-99m.

The macroaggregated particles prepared according to the method of this invention are sized between about 3 microns and about 150 microns in diameter, preferably between about 10 microns and about 90 microns in diameter, a majority being about 50 microns in diameter. The $^{99m}$Tc labeled MAA-stannous tartrate compound is useful in lung function studies. After injection into the patient, the macroaggregated particles are retained by the capillary system of th lungs, allowing a scintiphoto of the physiological vascular system of the lungs to be made. Macroaggregated particles of human serum albumin are non-toxic and readily digestible in the capillaries by the phagocytes. As a result, the obstruction of capillaries is of comparatively short duration.

Macroaggregated particles larger than 150 microns in diameter cause difficulties by blocking off large capillaries which is harmful to the pulmonary system. When macroaggregated particles are smaller than 3 microns in diameter, they pass through the capillaries directly to the liver. Moreover, even in the proper size range, the particles should be stable enough so that they do not break down and are not promptly released into the liver and spleen. Particles which pass immediately into the liver cause shadows and distort the scintiphoto of the lungs. Macroaggregated particles prepared according to the method of this invention and labeled with $^{99m}$Tc have been found to have a lung to liver ratio of particle distribution greater than about 100 to 1, i.e., less than about 1 percent of the particles passing into the liver. This percentage of particles passing into the liver is well below acceptable human tolerance levels.

In one aspect, this invention relates to a process for the preparation of a stable, non-radioactive carrier comprising stannous tartrate and a sequestering agent selected from the group consisting of a phosphorus-containing compound which contains a P—O—P linkage and a phosphonate which contains P—C—P bonds. Suitable sequestering agents include sodium polyphosphate, sodium phyrophosphate or any of a variety of phosphonates with hydroxyl, methyl, ethyl andchloro groups substituted for hydrogen on the carbon atom. As described hereinbefore, a preferred sequestering agent in HEDSPA having the following structure:

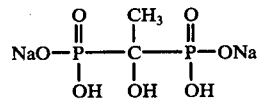

According to the method of this invention a sequestering agent as defined hereinabove such as HEDSPA is contacted with a sufficient amount of nonoxidizing acid to form a solution having a pH from about 2 to about 7, preferably about 6.0. Suitable nonoxidizing acids include hydrochloric, acetic, sulfuric and phosphoric and the like. Preferably, a 1 Normal hydrochloric acid is employed. Stannous tartrate is dissolved in this solution and the resulting solution has a pH between about 2 and about 7, but preferably about 4. Preferably, stannous tartrate is added to the solution containing the sequestering agent such as a HEDSPA-solution in an amount between about 3 to 1 and 20 to 1 of sequestering agent such as HEDSPA to stannous tartrate on a weight basis. The final pH of the solution may be adjusted by using sodium hydroxide solution. The solution may be lyophilized at a temperature below 0° C, preferably between about 0° C and −10° C when it is desirable to store it before use, or it may be used in liquid form for a short time.

$^{99m}$Tc labeled HEDSPA may be prepared by contacting the lyophilized or liquid product with a sufficient amount of a saline solution of Na$^{99m}$TcO$_4$ to form $^{99m}$Tc-HEDSPA solution.

In another aspect, this invention relates to a method of preparing a non-radioactive macroaggregated albumin product. A saline solution is acidified to a pH between about 2 and about 6, preferably about 5.5 with a sufficient quantity of a non-oxidizing acid. Suitable non-oxidizing acids include hydrochloric, acetic, sulfuric, phosphoric or the like. A preferred acid is hydrochloric acid. Stannous tartrate is dissolved in the solution and then Human Serum Albumin is added, or this order of addition may be reversed, if desired. The pH of the resulting solution may then be adjusted with the addition of a sufficient amount of sodium hydroxide to between 5 and about 6, but preferably between about 5.5 and about 5.6. After adjusting the pH, the solution is heated a predetermined time between about 20 minutes and about 40 minutes, preferably about 25 minutes, at a temperature sufficient to macroaggregate the albumin. This temperature may range between about 70° C and about 80° C, but preferably is about 74° C.

Preservatives may be used in the method of this invention, but are not necessary for the efficacy of the product. Suitable preservatives include thimersal, parabens (methyl p-hydroxybenzoates and propyl p-hydroxybenzoates) and the like. Generally, the preservative may be added during the preparation of the stable, non-radio-active carrier product of this invention. The product may be prepared in the wet form or lyophilized at a temperature below about 0° C, preferably between about 0° C and about −10° C.

This stable, non-radioactive product of macroaggregated albumin formed as described hereinabove may be labeled with technetium-99m by contacting the lyophilized or liquid product with a sufficient amount of a saline solution of Na$^{99m}$TcO$_4$ to form $^{99m}$Tc macroaggregated albumin solution. The $^{99m}$Tc-labeled MAA product should have a radioactivity concentration of at least about 1 millicurie (mCi) per unit volume of solution. Typically, between about 0.5 ml and about 1 ml of solution woulld be administered to patients when using the solutions for radiodiagnostic testing purposes.

In still another aspect, this invention relates to a method for the preparation of a suitable non-radioactive human serum albumin. A predetermined amount of stannous tartrate is dissolved in a predetermined amount of non-oxidizing acid and diluted with an aqueous solution to form a stannous tartrate containing solution having a pH from about 2 to about 4. Suitable non-oxidizing acids include hydrochloric, acetic, sulfuric, phosphoric and the like. Preferably, hydrochloric acid is employed and particularly preferred is concentrated hydrochloric acid. The aqueous solution may be water or saline solution which is substantially free of molecular oxygen such as entrained or dissolved oxygen. For example, the water may be purged with nitrogen gas to remove molecular oxygen.

A predetermined amount of human serum albumin is diluted with an aqueous solution,, water or saline solution for example, the aqueous solution being substantially free of molecular oxygen such as entrained or dissolved oxygen and the pH of the HSA solution is adjusted to between about 2 and about 4, preferably about 3. The stannous tartrate containing solution is then contacted with the pH adjusted HSA solution to form a product solution. The pH of the product solution may be adjusted to between about 2 to about 4, preferably about 3 with a suitable base such as sodium hydroxide or HSA which acts as a buffer. If desired, the pH of the product solution may first be adjusted, prior to this final step, to between about 2 and about 4, preferably about 2.5 with a non-oxidizing acid, preferably hydrochloric acid.

The final pH adjusted product solution may be lyophilized at a shelf temperature between 0° C and about 30° C, and preferably at about 20° C for time sufficient to yield a dry product. The ratio by weight of the HSA to the stannous tartrate in the final product solution or lyophilized product should be between about 50 to 1 and about 150 to 1, preferably about 100 to 1.

In another aspect of this invention, $^{99m}$Tc-labeled HSA may be prepared by following the method described previously for preparing a non-radioactive HSA-stannous tartrate solution or lyphilized product and then contacting the HSA-stannous tartrate solution or lyophilized product with a sufficient amount of a saline solution of Na$^{99m}$TcO$_4$ to form $^{99m}$Tc-HSA solution. A preferred method of preparing a $^{99m}$Tc-labeled HSA product is as described previously for the preparation of the non-radioactive lyophilized HSA-stannous tartrate product, reconstituting with an amount of water sufficient to replace the amount of water removed during lyophilization and then contacting the resulting solution with sufficient amount of a saline solution of Na$^{99m}$TcO$_4$ to form $^{99m}$Tc-HSA solution.

The following examples illustrate the invention:

EXAMPLE 1

Two parallel runs were made using the identical procedure in each case, except that stannous chloride was used as the reducing agent in one run and in the other run stannous tartrate was used as the reducing agent in the preparation of a MAA lung scanning agent. The following procedure was used:

In one run 30 mg of stannous chloride in 2 ml (approximately 0.24 mg Sn++/ml) 0.1 N HC1 was added to 90 ml of normal saline solution. In the other run, 50 mg of stannous tartrate (approximately 0.24 mg Sn++/ml) in 2 ml of 0.1 N HC1 was added to 90 ml of normal saline solution. 0.25 ml of 25 percent human serum albumin (HSA) was then added to the saline solution. The pH of the solution was adjusted to 5.5 with 0.1 N NaOH. After the solution was incubated at a temperature of 21° C for 15 minutes, the albumin was denatured at 74° C for 25 minutes. 0.6 ml aliquots of macroaggregates in saline solution prepared as described above were transferred to 10 ml serum vials. The vials were centrifuged and the supernate decanted.

Use of the stannous tartrate reducing agent produced macroaggregated albumin particles which make a superior lung scanning agent. It did not produce large particles and the lung to liver ratio was very good. It is necessary that the lung to liver ratio be at least 20 to 1 with no particles greater than 150 microns in order that the lung scanning agent meet standard specifications. A comparison between MAA made using stannous chloride and stannous tartrate indicated MAA made using stannous chloride could not meet these standard specifications. A comparison between the two systems is summarized in Table I below:

TABLE I

Comparison Study Between Stannous Chloride and Stannous Tartrate in the Preparation of a MAA Lung Scanning Agent

| Comparison Test | Stannous Chloride | Stannous Tartrate |
|---|---|---|
| Lung to Liver Ratio | 12 to 1 | 200 to 1-295 to 1 |
| % Activity in Lung | 94 | 96.5 |
| *Total Number of particles/ml | 200,000 | 3,000,000 |
| Particle Size | Majority of particles between 150-200 microns | More than 80% between 30-70 microns less than 4% under 10 microns none over 100 microns |
| Toxicity in Mice | Labored breathing, sluggishness, probably death would result | No reaction |

*This number represents total number of particles before tagging with 3 ml of $^{99m}$Tc.

A further comparison was made using 0.6 ml aloquots of macroaggregates in saline solution prepared with stannous tartrate as described hereinabove in this example and placed in serum vials, centrifuged and decanted. In one group, the MAA particles in the vials were lyophilized and stored under refrigeration. In another group, the MAA particles in the vials were refrigeratored only, but not lyophilized in order to measure the effect of lyophilizing on shelf-life stability. 3 ml of low concentration $^{99m}$Tc was added to each vial containing MAA stannous tartrate chelate. The vials were shaken and incubated for 30 minutes at a temperature of 21° C. Although the freeze-dried samples were excellent lung to liver ratios if used immediately after preparation, on standing, there was a deterioration of the protein. This deterioration is believed to be caused by residual sodium chloride present in solution. After 18 days, the freeze-dried samples gave unsatisfactory lung to liver ratios. Moreover, the freeze-dried samples had the further disadvantage of adherence to the bottom of the vials after storage, making it difficult to resuspend the particles. In constrast, the centrifuged samples did not have this sticking problem and gave good lung to liver ratios even after 18 days. The results are summarized in Table II below:

TABLE II

Shelf-Life Study on Freeze-Dried and Centrifugated MAA Particles

| | Lung to Liver Ratio | |
|---|---|---|
| Time After Preparation (Days) | Freeze-Dried After Centrifugation | Centrifuged Only |
| 4 | 245 to 1 | 220 to 1 |
| 8 | 129 to 1 | 129 to 1 |
| 9 | 73 to 1 | 91 to 1 |
| 10 | 85 to 1 | 320 to 1 |
| 11 | 46 to 1 | 166 to 1 |
| 15 | 28 to 1 | 318 to 1 |
| 18 | 25 to 1 | 216 to 1 |

EXAMPLE 2

A macroaggregated albumin-stannous tartrate chelate useful in lung scanning applications may be prepared according to this invention as follows: A minimum of 20 mg and a maximum of 100 mg of stannous tartrate is dissolved in approximately 2 ml of 0.1 N HCl and 90 ml of normal saline solution. 0.25 ml of 25 percent human serum albumin is added and the pH is adjusted to 5.5 with 0.1N NaOH. 8 ml of normal saline is added to this solution and the pH readjusted to 5.5 with 0.1N HCl if necessary. This solution is filtered through a 0.22 micron filter. The filtered solution is diluted to approximately 110 ml with normal saline and placed in a temperature controlled bath at 74° C for 25 minutes. 0.6 ml aliquots are transferred to 10 cc vials and centrifuged for 1.5 minutes. The supernate is decanted. To prepare the $^{99m}$Tc-MAA particles for lung scanning, 3 ml of pertechnetate (Na $^{99m}$TcO$_4$) saline solution is added to the vial containing the centrifuged particles and, after 30 minutes incubation at a temperature of 21° C, the radiodiagnostic product is ready for use.

Reagents prepared as described hereinabove in this example have shown lunt-to-liver ratios of greater than 200 to 1 in bioassay tests in mice. Binding of the $^{99m}$Tc to the particles was greater than 90 percent as determined by paper chromatography. Stability of the MAA-stannous tartrate particles (non-radioactive chelate) was measured to be at least 120 days and the stability of the $^{99m}$Tc-tagged MAA particles (radiodiagnostic agent) was greater than 6 hours. More than 80 percent of the particles were in the 30-70 micron size range with no particles having a size greater than 100 microns.

EXAMPLE 3

Using the following procedures, two non-radioactive chelates, HEDSPA-stannous chloride and HEDSPA-stannous tartrate were prepared for comparison of stability and shelflife.

A batch of 150 ml of HEDSPA-stannous chloride, the final reagent, was prepared as follows: 75 ml of HEDSPA (5mg/ml) were added to a 500 ml flask which was purged with nitrogen gas. 53.8 cc of 0.2 N HCl were added to the flask which was purged with nitrogen gas again for about 2 hours. 3.7 ml of stannous chloride solution in 0.2N HCl (10.4 mg SN++/ml) were added to the flask and mixed. 14 ml of 1.0 N NaOH was added to the flask and mixed so that the final reagent had a pH of 4.0 (0.25 mg Sn++/ml). 1 ml of the final reagent was dispensed into 10 ml serum vials which were placed in a freeze dryer and lyophilized at −40° C and 200 microns of Hg vacuum for 48 hours.

A batch of 200 ml of the final reagent, HEDSPAstannous tartrate, was prepared as follows: 100 ml of HEDSPA (5 mg/ml) were added to 250 ml flask which was purged with nitrogen gas. The pH was adjusted to 6.0 with 0.2 N HCl.116 mg of solid stannous tartrate was added to the flask and mixed until dissolved. The solution in the flask was diluted to 200 ml with distilled water until the solution contained 0.25 mg Sn++ml and had a final pH of 4.0. 1 ml of the final reagent was dispensed into 10 ml serum vials which were placed in a freeze dryer and lyophilized at −40° C and 200 microns of Hg vacuum for 48 hours.

The two final reagents were analyzed immediately and stored for various time periods. A technetium-99m radiodiagnostic agent useful for bone scanning was prepared by the addition of 3 ml of sodium pertechnetate (Na$^{99m}$TcO$_4$) containing 30 mCi of $^{99m}$Tc to the final reagents, respectively, which were then shaken for 1 minute. The percent binding efficiency of the chemical labeling procedure and stability of the preparation were determined by ascending paper chromatography using Whatman No. 1 paper strips in 85 percent methanol and scanning on a radiochromatographic scanner. The bioassay in mice was determined by injecting 0.2 ml into the tial veins of mice and sacrificing them after 1 hour uptake times. Table III below summarizes that data;

TABLE III

Shelf-Life Study on HEDSPA - SnCl₂ and HEDSPA-Sn-Tartrate at pH 4.0

| | Time After Preparation (Days) | % Binding | *Bioassay in Mice % of Injected Activity | | | | |
|---|---|---|---|---|---|---|---|
| | | | Body | Intestines | Liver | Kidney | Heart and Lungs |
| STANNOUS CHLORIDE | 1 | 99 | 81.4 | 4.1 | 0.7 | 2.0 | 0.2 |
| | 5 | 93.5 | 86.6 | 7.5 | 1.8 | 3.4 | 0.3 |
| | 8 | 91.4 | 93.8 | 3.1 | 1.1 | 1.9 | 0.2 |
| | 21 | 21.8 | 33.9 | 33.6 | 26.4 | 26.4 | 1.0 |
| | 35 | 3.3 | NO BIOASSAY PERFORMED | | | | |
| STANNOUS TARTRATE | 3 | 99 | 89.9 | 7.2 | 0.8 | 2.0 | 0.2 |
| | 4 | 99 | 93.8 | 3.3 | 1.0 | 1.8 | 0.2 |
| | 12 | 99 | 91.4 | 5.2 | 1.0 | 2.0 | 0.4 |
| | 21 | 99 | 92.7 | 5.2 | 0.8 | 1.2 | 0.1 |
| | 37 | 99 | 93.0 | 4.4 | 0.6 | 1.6 | 0.3 |
| | 50 | 99 | 93.2 | 2.7 | 1.0 | 2.6 | 0.5 |
| | **78 | 99 | 94.6 | 1.86 | 0.81 | 1.72 | 0.21 |

*Average of two mice, 1 hour uptake.
**Average of three mice, 0.2 cc injection.

The results of Table III above indicates that HEDSPA-SnCl₂ at pH 4.0 loses its binding capacity between about 8 and about 21 days, rendering it undesirable as a non-radioactive chelate intermediate in the production of a technetium-99m labeled radiodiagnostic agent due to its short shelf-life. This is reinforced by the results of the bioassay on mice wherein the liver uptake after 21 days storage was undesirably high. In contrast, the HEDSPA-stannous tartrate at pH 4.0 retained its binding capacity after 78 days with little or no uptake in the liver. In still another shelf-life study, a batch of lyophilized HEDSPA-stannous tartrate at pH 4.0 was reconstituted using 3 ml of high concentration $^{99m}$Tc with satisfactory bioassay and binding results.

EXAMPLE 4

Four salts of stannous compounds were each dissolved in a solution of 40 ml of saline and 1 ml of 1N HCl which was purged with nitrogen. The stannous concentrations was measured and then the solution was subjected to oxidation conditions by bubbling air through the solution for 2.5 hours. The stannous concentration was again measured. The results indicated that stannous tartrate is much more stable to air oxidation than stannous chloride. Moreover, the presence of tartaric acid does not significantly improve the stability of the stannous chloride, even when present in excessive amounts. The results are summarized in Table IV below:

TABLE IV

Comparison Tests on the Stability of Stannous Compounds to Air Oxidation

| Salt Sample | Stannous Concentration Before Aeration (mg/ml) | Stannous Concentration After Aeration (mg/ml) | % Stannous Tin Remaining |
|---|---|---|---|
| 1. Stannous Chloride + Tartaric Acid (Equivalent amount of tartaric) | 10.8 | 6.0 | 55.5 |
| 2. Stannous Chloride + Tartaric Acid (twice equivalent amount of tartaric) | 10.4 | 4.2 | 40.4 |
| 3. Stannous Chloride | 9.3 | 3.6 | 38.7 |
| 4. Stannous Tartrate | 18.0 | 17.0 | 94.5 |

EXAMPLE 5

Six salts of stannous compounds were each dissolved in 98 ml of saline containing 2 ml 1N HCl. The solutions were analyzed in order to measure the stannous ion concentration and then were subjected to oxidation conditions by bubbling air through the solutions for one hour. The solutions were analyzed again. The results indicated that stannous tartrate is more stable than stannous chloride with tartrate or citrate ion present. Table V below summarized the results:

TABLE V

Comparison Tests on the Stability of Various Stannous Compounds to Air Oxidation

| Salt Sample | Stannous Concentration Before Aeration (mg/ml) | Stannous Concentration After Aeration (mg/ml) | % Not Oxidized Tin |
|---|---|---|---|
| 1. Stannous Chloride | 0.138 | 0.085 | 61.6 |
| 2. Stannous Tartrate | 0.247 | 0.213 | 86.2 |
| 3. Stannous Chloride + Stannous Tartrate | 0.151 | 0.003 | 19.3 |
| 4. Stannous | | | |

TABLE V-continued

Comparison Tests on the Stability of Various
Stannous Compounds to Air Oxidation

| Salt Sample | Stannous Concentration Before Aeration (mg/ml) | Stannous Concentration After Aeration (mg/ml) | % Not Oxidized Tin |
|---|---|---|---|
| Chloride + Potassium-Sodium Tartrate | 0.166 | 0.002 | 15.0 |
| 5. Stannous Chloride + Sodium Oxalate | 0.134 | 0.002 | 15.0 |
| 6. Stannous Chloride + Sodium Citrate | 0.196 | 0.092 | 47.0 |

EXAMPLE 6

A non-radioactive carrier solution, HSA-stannous tartrate was prepared in the following manner: 158 mg of stannous tartrate was dissolved in 0.3 ml of concentrated HCl and diluted to 190 ml with water. The solution was stirred and purged with nitrogen gas for a minimum of 20 minutes. 40 ml of 25 percent human serum albumin (HSA) was diluted to 60 ml with water and stirred for 5 minutes. The pH of the HSA solution was adjusted to 3 using 1.0N HCl added slowly dropwise using a pipetting buret and stirring for 5 minutes. The stannous tartrate solution was filtered through a 0.22 micron filter; 140 ml of the filtered solution was added to the HSA solution; and purged with nitrogen gas for 40 to 45 minutes. The pH of the resulting solution was then adjusted to 2.5 with 1.0N HCl. The final pH of the so-formed solution was adjusted to 3 with additional HSA. The final pH adjusted solution was dispensed into serum vials through a sterile 0.22 micron filter and freezed dried using a shelf heat of 20° C to form a lyophilized reagent.

$99m$Tc radiodiagnostic agent suitable for blood pool scanning or cardiac studies was prepared by reconstituting the lyophilized reagent with 1 ml of water. Then 3 ml of Na$^{99m}$TcO$_4$ was added. 0.2 cc of the tagged reagent was injected into mice and a bioassay was performed after 30 minutes. The results of the bioassay in mice are shown in Table 6 hereinbelow:

TABLE 6

$99m$Tc-HSA

Biossay in Mice After 30 Minutes

| Organ | % of Total Activity in Mice |
|---|---|
| Blood | 56 |
| Intestines and Stomach | 10.7 |
| Liver | 12.7 |
| Kidney | 5.1 |

A criterion for a good blood pool agent is having 45–65 percent activity in the blood of mice 30 minutes after injection. See for example, Rhodes, B.A., Seminars in Nuclear Medicine, Vol. 4, No. 3, pp. 281–293 (1974).

Urine clearance was measured over a longer period by holding mice in metabolic cages and collecting the urine washings. After 6 hours, 37 percent of the injected dose had been cleared via the urine. After 24 hours, 50 percent had been excreted.

EXAMPLE 7

In this example, stannous chloride was used in place of stannous tartrate for comparison purposes. 63 mg of stannous chloride were dissolved in 100 ml of normal saline, to which 1.5 ml of 1N HCl were added while purging with nitrogen gas. The stannous solution was passed through a 0.22 μ membrane filter to separate out any undissolved stannic particles. The pH of 2 cc of human serum albumin was adjusted to 3.0 with 1 N HCl, dropwise. 10 ml of the stannous solution were added to the HSA solution which was stirred and purged with nitrogen for 20 minutes. After adding the stannous solution to the pH 3.0 HSA solution, the resultant solution was again filtered through a 0.22 μ Millipore filter to prevent any increased liver/lung uptake due to particles or colloidal material which may be formed in the solution due to pH adjustments. For immediate testing 0.5 ml of the product solution were mixed with 2 ml of low-concentration $99m$TcO$_4^-$. For lyophilization, the product solution was aliquoted into 0.5 cc fractions and freeze dried. 2 ml of low-concentration $99m$TcO$_4^-$ were also used to reconstitute the lyophilized product.

Bioassay results using the SnCl$_2$ solution showed 55 percent of the $99m$Tc activity in the blood pool after 30 minutes, which is about the same as a stannous tartrate-HSA- solution. However, when the SnCl$_2$ reagent was lyophilized at a pH of 3.0 and 3.5 and then rehydrated with 3 ml of low-concentration $99m$TcO$_4^-$, the activity remaining in the blood pool of mice after 30 minutes dropped to 46 percent and 44 percent, respectively. A similar procedure with stannous tartrate resulted in a reagent which showed less degradation after lyophilization and rehydration. The shelf-life is also extended when using stannous tartrate as the reducing agent as compared to stannous chloride.

EXAMPLE 8

Using the procedure described previously in Example 7 except substituting stannous tartrate for stannous chloride, a study was made to determine the effect of pH from 3.0 to 4.0 on the Sn-tartrate-HSA reagent. Results for the lyophilized products (0.5 cc of Sn-tartrate-HSA to which 2 cc of low-concentration $99m$TcO$_4^-$ were added) are shown in Table VII below:

TABLE VII

Sn-Tartrate-HSA (NaOH Adjusted) at
pH 3.0–4.0, Average* % in Blood
of Mice 30 minutes after Injection

| | % of Recovered Activity in Mouse's Blood Pool 30 Minutes After Injection | |
|---|---|---|
| pH | Wet | Lyophilized |
| 3.0 | 55 | 55 |
| 3.3 | 47 | — |

TABLE VII-continued

Sn-Tartrate-HSA (NaOH Adjusted) at
pH 3.0-4.0, Average* % in Blood
of Mice 30 minutes after Injection

| pH | % of Recovered Activity in Mouse's Blood Pool 30 Minutes After Injection | |
|---|---|---|
|  | Wet | Lyophilized |
| 3.5 | 45 | 45 |
| 4.0 | 39 | — |

*Average percent of 4 mice.

EXAMPLE 9

Three batches of a non-radioactive stannous tartrate-HSA reagent were prepared using the following procedure: 63 mg of stannous tartrate were dissolved in 1.5 ml of 1N HCl and stirred for 30 minutes. 2 cc of sterile water were added to the solution which was stirred for 20 minutes. The solution volume was adjusted to 100 ml with sterile coater, stirred for 15 minutes and passed through a 0.22 micron membrane filter. The pH of 2.0 ml of a human serum albumin (HSA), 25 percent salt poor, was adjusted at 0-4° C to 3.5 by adding 1N HCl dropwise and stirring for 10 minutes. The pH was then readjusted to 3.0 by adding additional 1N HCl dropwise; total 1N HCl used is 0.86-0.90 cc. 10 ml of the stannous tartrate solution was added to the HSA solution which was being purged with nitrogen. The resultant solution was stirred for 25 minutes. The pH of the solution was then adjusted to 3.0 using 0.5 ml HSA and filtered through an 0.22 micron membrane filter.

The non-radioactive Sn-tartrate HSA reagent so prepared was used wet when 0.5 ml of the reagent were added to 2 ml of low-concentraion $^{99m}TcO_4^-$. The re-agent was also used in lyophilized form when 0.5 ml aliquots were freezedried, then rehydrated with 2 ml of low-concentration $^{99m}TcO_4^-$. Lyophilization was accomplished by pre-freezing the product at −10° C to −15° C and then lyophilizing overnight with the shelf temperature set to −100° F and the condenser at −60° F.

In each of the batches, however, modifications were made. In the first two batches, the stannous tartrate was dissolved in normal saline whereas in the third batch, it was dissolved in water. Moreover, in the first batch, NaOH was employed for pH adjustment to 3.0 whereas in the second and third batch, HSA was employed for pH adjustment.

The three batches were tested in mice and test results are summarized in Table VIII. The results are the percent of the recovered activity in the blood of a 20-26 gm mouse 30 minutes after injection. From the activity in the collected blood pool, the total activity in the blood was projected assuming the 7 percent of the mouse's body weight is blood. The average results for the three batches are shown in Table VIII hereinbelow.

TABLE VIII

Effectiveness of Several HSA Reagents
in Mic-Comparative Average Data

| Batch | Type Product | pH | % of Recovered Activity in Blood 30 Minutes after Injection |
|---|---|---|---|
| Sn Tartrate in Normal Saline; NaOH for pH Adjustment | Wet | 3.0 | 55.2 |
| | Lyophilized | 3.0 | 52.1 |
| | Wet | 4.0 | 46.1 |
| | Lyophilized | 4.0 | 45.9 |
| Sn Tartrate in Normal Saline; HSA for pH Adjustment | Wet | 3.0 | 59.5 |
| | Lyophilized | 3.0 | 52.9 |
| Sn Tartrate in H$_2$O for pH Adjustment | Wet | 3.0 | 56.5 |
| | Lyophilized | 3.0 | 55.3 |

EXAMPLE 10

A 270 ml batch of Sn-Tartrate-HSA reagent was prepared as follows: 158 mg of stannous tartrate was added to 3.75 ml of 1N HCl and the solution stirred for 1 hour. 4 ml of water were added for injection and stirred for 15 minutes. The volume of the stannous tartrate solution was adjusted to 250 ml with water for injection and the solution was stirred for 20 minutes while being purged with nitrogen. The Sn-tartrate solution was then passed through an 0.22 micron filter into a sterile container.

40 ml. of normal human serum albumin, 25 percent (salt poor), under refrigeration at about 40° C was dispensed into a 300 ml beaker. The pH of the HSA soltuion was adjusted to 3.4± 0.1 with 1 N HCl dropwise and stirred for 5 minutes. The pH of the HSA solution was then lowered to 3.15± 0.05 by adding 1N HCl dropwise (total HCl about 18 ml). 200 1 ml of the strannous tartrate solution was slowly added to the HSA solution and stirred for 40 minutes. The Sn-tartrate-HSA was then continuously purged with nitrogen. The pH of the Sn-tartrate-HSA solution was adjusted to 2.9± 0.05 by adding an additional 6.0-7.0 of HSA. The Sn-tartrate-HSA solution was diluted to 270 ml with water for injection and stirred for 5 minutes. 0.5 ml aliquots were dispensed through a 0.22 μ filter into sterile 10 cc serum vials and lyophilized at a shelf temperature of 20° C for 24 hours. Per vial, the ratio by weight of HSA stannous tartrate was 21.5 mg of HSA to 0.23 mg of stannous tartrate.

The batch was rehydrated using 2 ml of low concentration $^{99m}TcO_4^-$ per vial. 0.5 ml was injected intravenously into laboratory animals (rabbit and guinea pig). Blood was collected directly from the heart by syringe, and 0.5 ml standard of $^{99m}$Tc-HSA was the basis for the calculations. The results of a bioassay are summarized in Table IX below:

TABLE IX

Guinea Pig and Rabbit Bioassay
30 Minutes After Injection

| Organ | % of Injected Activity | |
|---|---|---|
| | Rabbit | Guinea Pig |
| Blood Pool | 79 | 69 |
| Stomach | 0.7 | 0.6 |
| Intestines | 3.3 (small), 1.3 (large) | |
| Spleen | 0.2 | — |
| Liver | 9.3 | 9.5 |
| Lung | 2.1 | 1.2 |
| Kidney | 6.5 | 4.0 |
| Heart | 2.1 | 1.1 |
| Bladder (Full) | 5.8 | — |

As can be seen from the data above, 69-76 percent of the injected $^{99m}$Tc (HSA) is in the blood pool after 30 minutes; and the stomach activity is nearly nil, and the intestinal activity is extremely low (~3%).

EXAMPLE 11

A number of vials of HSA reagent prepared as described in Example 10 were tested for solubility in volumes of isotonic saline greater than 1 milliter. The pharmacology of the reagent was preserved when dissolved in 2-6 ml of low concentration $^{99m}$TcO$_4^-$ and 1-3 ml of high concentration $^{99m}$TcO$_4^-$. A bioassay showing the average percentage in the blood of at least two mice per point is summarized in Table X hereinbelow:

TABLE X

Average % of Injected Activity in the Blood of Mice 30 Minutes after Injection (HSApH3.0)

| Volume | mCi/ml | | |
|---|---|---|---|
| | 10 | 30 | 100 |
| 1 | * | 55 | * |
| 2 | 56 | 54 | * |
| 3 | 55 | 56** | 53** |
| 6 | * | * | * |

*not tested
**tagging time = 45 minutes

The date above shows that the tagged HSA reagent of this invention has flexibility in its range of solubility. Also, radiation degradation is no problem, since, as shown above, 100 mCi/ml or 300 mCi/ml total did not change the pharmacology of the $^{99m}$Tc-HSA. Moreover, microscopic examination has shown no unsafe particle formation in the product reagent of this invention. And the Sn-tartrate-HSA lyophilized reagent has been stored at room temperature for 63 days, reconstituted with water, tagged with $^{99m}$Tc and injected in mice. Bioassay tests in mice 30 minutes after injection showed more than 53 percent of recovered activity in the blood pool with no degradation in the reagent due to storage conditions or time

EXAMPLE 12

A batch of Sn-tartrate-HSA lyophlized reagent was prepared using the procedure described in Example 6. The reagent was constituted with a 1 ml water addition and tagged with 30mCi/ml $^{99m}$Tc. Mice were administered the $^{99m}$Tc-HSA at 30 minutes and 6 hours after tagging, sacrificed after 30 minutes, and the stability determined by paper chromatographic analyses. The amount $^{99m}$Tc bound to the HSA will determine the amount of the product reagent.

A measure volume of tagged product was deposited about 3 cm from one end of a strip of Whatman No. 1 paper and allowed to dry. The chromatogram was developed in 85 percent methanol for a period of about 3 hours by ascending chromatography. The radioactivity distribution was determined by scanning the chromatogram in a radiochromatograph scanner. From the ratio of radioactivity of the band at the origin to the total radioactivity (origin and at R$_f$ 0.65-75 $^{99m}$TCO$_4^-$), the percent binding was calculated. Paper chromatographic analyses indicated that 30 minutes after tagging, the $^{99m}$TC-HSA product of this invention was 98 percent $^{99m}$TC bound, and 6 hours after tagging it was 96 percent $^{99m}$Tc bound.

Those skilled in the art will appreciate that the particular examples of this invention described hereinabove are intended to be illustrative only and are not intended to limit the scope of the invention.

What is claimed is:

1. A stable, non-radioactive carrier suitable for cardiac studies, blood pool and brain scanning when labeled with $^{99m}$TC, said carrier comprising human serum albumin (HSA) and strannous tartrate, the ratio by weight of said HSA to stannous tartrate being between about 50 to 1 and about 150 to 1.

2. A carrier as defined in claim 1 wherein said ratio is about 100 to 1.

3. A method of preparing a stable, nonradioactive carrier suitable for cardiac studies, blood pool and brain scanning when labeled with $^{99m}$Tc, said method comprising:
   dissolving stannous tartrate in a non-oxidizing acid to form a stannous tartrate solution;
   adjusting the pH of said stannous tartrate solution to a pH between about 2 and about 4;
   adjusting the pH of a human serum albumin (HSA) solution to a pH between about 2 and about 4;
   contacting said stannous tartrate solution with said HSA solution to form a stannous tartrate-HSA solution; and
   adjusting the pH of said stannous tartrate-HSA solution to between about 2 and about 4.

4. A method as defined in claim 3 wherein the pH of said stannous tartrate-HSA solution is adjusted with the addition of a pH adjusting solution selected from the group consisting of sodium hydroxide and human serum albumin.

5. A method as defined in claim 4 wherein said pH adjusting solution is human serum albumin.

6. A method as defined in claim 3 wherein the pH of said stannous tartrate solution is (said) adjusted with an aqueous solution which is substantially free of entrained or dissolved oxygen.

7. A method as defined in claim 6 wherein said aqueous solution is water or sodium hydroxide.

8. A method as defined in claim 3 further including before said stannous tartrate solution is contacted with said HSA solution;
   adjusting the pH of said HSA solution to about 3.

9. A method as defined in claim 3 further including after said stannous tartrate solution has been contacted with said HSA solution;
   adusting the pH of said HSA solution to about 2.5 with a non-oxidizing acid.

10. A method as defined in claim 3 wherein said non-oxidizing acid is selected from the group consisting of hydrochloric, acetic, sulfuric and phosphoric acid.

11. A method as defined in claim 10 wherein said non-oxidizing acid is hydrochloric acid.

12. A method as defined in claim 11 wherein said non-oxidizing acid is concentrated hydrochloric acid.

13. A method as defined in claim 3 further including after the pH of said stannous tartrate-HSA solution is adjusted to between about 2 and about 4;
   lyophilizing said stannous tartrate-HSA solution at a shelf temperatue between about 0° C and about 30° C to form a solid.

14. A method as defined in claim 13 wherein said shelf temperature is about 20° C.

15. A method as defined in claim 13 further including after said lyophilization of said stannous tartrate-HSA solution;

redissolving said lyophilized solid with an amount of aqueous solution sufficient to replace the water removed during said lyophilization step; and contacting said redissolved solution with a sufficient amount of a saline solution of Na$^{99m}$TcO$_4$ to form a $^{99m}$Tc-labeled radiodiagnostic agent suitable for cardiac studies, blood pool and brain scanning.

16. A method as defined in claim 3 further including after said pH adjustment of said stannous tartrate-HSA solution;

contacting said stannous tartrate-HSA solution with a sufficient amount of a saline solution of Na$^{99m}$TcO$_4$ to form a $^{99m}$Tc-labeled radiodiagnostic agent suitable for cardian studies, blood pool and brain scanning.

17. A method as defined in claim 13 further including after said lyophilization of said stannous tartrate-HSA solution;

contacting said lyophilized solid with a sufficient amount of saline solution of Na$^{99m}$TcO$_4$ to form a $^{99m}$Tc-labeled radiodiagnostic agent suitable for cardiac studies, blood pool and brain scanning.

18. A radiodiagnostic agent suitable for cardiac studies, blood pool and brain scanning and having a pH between about 2 and about 4, said agent comprising a mixture of stannous tartrate, human serum albumin and a saline solutin of Na$^{99m}$TcO$_4$, the ratio by weight of said human serum albumin to said stannous tartrate being between about 50 to 1 and about 150 to 1.

19. An agent as defined in claim 18 wherein said ratio is about 100 to 1.

* * * * *